United States Patent
Vit et al.

[19]

[11] Patent Number: 6,059,971
[45] Date of Patent: May 9, 2000

[54] DEVICE AND PROCESS FOR THICKENING AND CONVEYING WASTE WATER SLUDGE

[76] Inventors: Robert Vit, Peter-Vischer-Str. 11, D-95615 Marktredwitz, Germany; Michal Dohanyos, Sochanova 1132; Jana Zabranska, Kozlovska 1a, both of 163 00 Praha 6, Czech Rep.; Josef Kutil, Machova 905, 250 01 Brandys Nad Labem-Stara Boleslay, Czech Rep.

[21] Appl. No.: 08/875,503

[22] PCT Filed: Jan. 30, 1996

[86] PCT No.: PCT/DE96/00130

§ 371 Date: Sep. 9, 1997

§ 102(e) Date: Sep. 9, 1997

[87] PCT Pub. No.: WO96/23736

PCT Pub. Date: Aug. 8, 1996

[30] Foreign Application Priority Data

Jan. 30, 1995 [DE] Germany ........................... 195 02 856
Jul. 28, 1995 [DE] Germany ........................... 195 27 784

[51] Int. Cl.[7] ........................... C02F 11/12; B01D 33/29; C12M 1/33; B04B 5/10
[52] U.S. Cl. ........................... 210/603; 210/609; 210/174; 210/374; 210/380.1; 210/396; 435/291.8; 435/306.1; 494/36; 494/48; 494/54; 494/73
[58] Field of Search ........................... 210/603, 605, 210/609, 613, 173, 174, 372–376, 380.1, 380.3, 381, 396; 494/36, 42, 48, 50–55, 58, 59, 73; 435/291.8, 298.2, 306.1

[56] References Cited

U.S. PATENT DOCUMENTS

| | | | |
|---|---|---|---|
| 2,600,372 | 6/1952 | Milliken | 233/7 |
| 3,735,920 | 5/1973 | Hausman | 494/50 |
| 3,955,756 | 5/1976 | Hiller | 494/53 |
| 4,085,887 | 4/1978 | Bye-Jørgensen et al. | 494/53 |
| 4,581,009 | 4/1986 | Krämer | 494/53 |
| 4,612,126 | 9/1986 | Alt et al. | 494/36 |
| 4,617,010 | 10/1986 | Epper et al. | 494/52 |
| 4,662,893 | 5/1987 | McIntosh | 210/174 |
| 4,731,182 | 3/1988 | High | 210/374 |
| 5,246,600 | 9/1993 | Reichner | 210/374 |
| 5,354,255 | 10/1994 | Shapiro | 494/53 |
| 5,670,047 | 9/1997 | Burke | 210/603 |

FOREIGN PATENT DOCUMENTS

| | | |
|---|---|---|
| GM 18 23 269 | 12/1960 | Germany. |
| AS 12 72 231 | 7/1968 | Germany. |
| 24 35 784 A1 | 2/1976 | Germany. |
| 28 22 533 A1 | 12/1978 | Germany. |
| 31 08 923 C2 | 11/1984 | Germany. |
| 33 01 099 A1 | 12/1984 | Germany. |
| 33 18 793 A1 | 1/1985 | Germany. |
| 34 28 535 A1 | 2/1986 | Germany. |

(List continued on next page.)

OTHER PUBLICATIONS

Abstract (D14), "Waste Water Purification in Munich II", 1986.
Abstract (D15), "Separators—Centrifuges for Clarification, Separation and Extraction", 1979.

*Primary Examiner*—Thomas G. Wyse
*Attorney, Agent, or Firm*—Pendorf & Cutliff

[57] ABSTRACT

The present invention relates to a device and a process for thickening and conveying waste water sludges, especially with a centrifuge. Here, the centrifuge has at least one lysis device for the breaking down of cells of organisms contained in the waste water sludges. The lysis device of the device of the invention may take the form, for example, of a friction grinder (100; 200) with grinding discs (161, 162) or a milling cone, a shaped rasp, a roller crusher, a passing drum, a cutting unit with rows of rotary cutters or a pin grinder with rows of rotating pins. The device of the invention is capable of the lysis of cells, especially those of bacteria and protozoons so that their cell content discharges into the surrounding medium which then acts as a simulation reagent for the bacteria still present in the sludge, so that on the one hand the total quantity of sludge can be greatly reduced and on the other the bio-gas yield is considerably increased.

62 Claims, 9 Drawing Sheets

FOREIGN PATENT DOCUMENTS

| | | |
|---|---|---|
| 39 19 176 A1 | 3/1990 | Germany . |
| 38 36 906 A1 | 5/1990 | Germany . |
| 40 41 162 A1 | 6/1992 | Germany . |
| 37 19 441 C2 | 2/1993 | Germany . |
| 43 06 337 A1 | 9/1993 | Germany . |
| 42 21 867 A1 | 1/1994 | Germany . |
| 34 24 615 C2 | 4/1994 | Germany . |
| WO 93/00562 | 1/1983 | WIPO . |

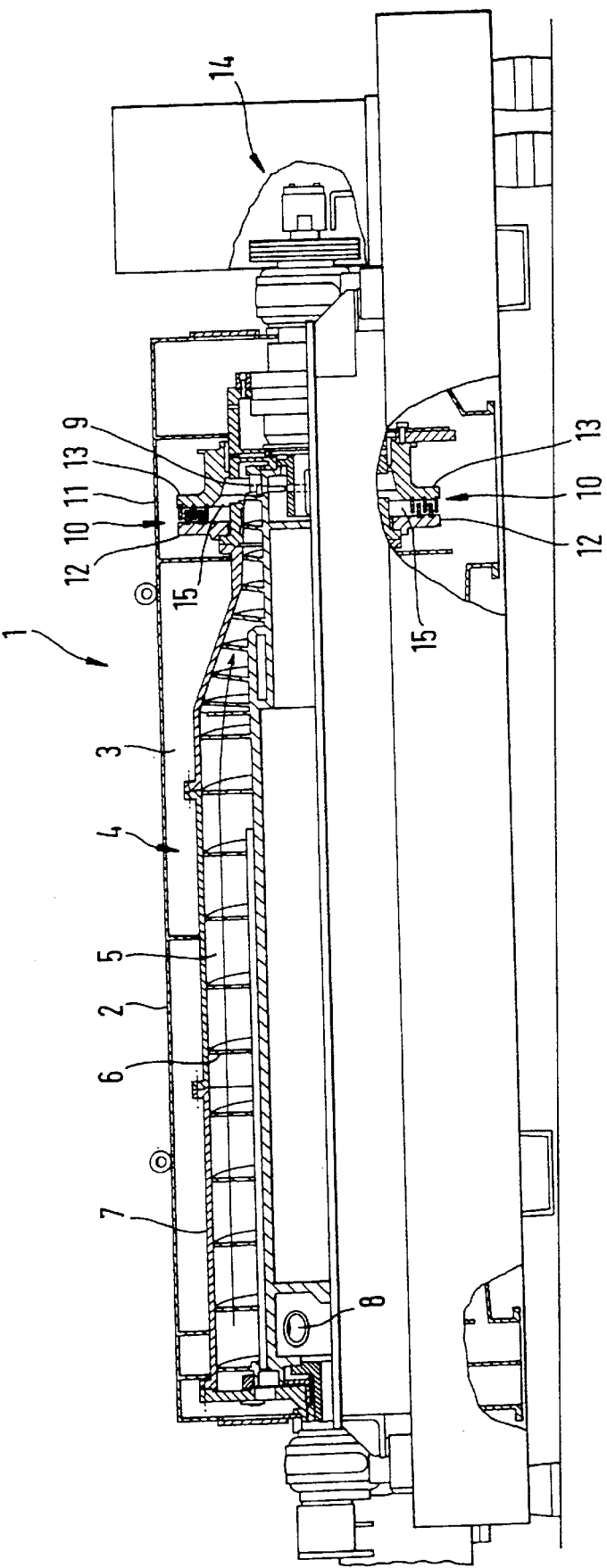

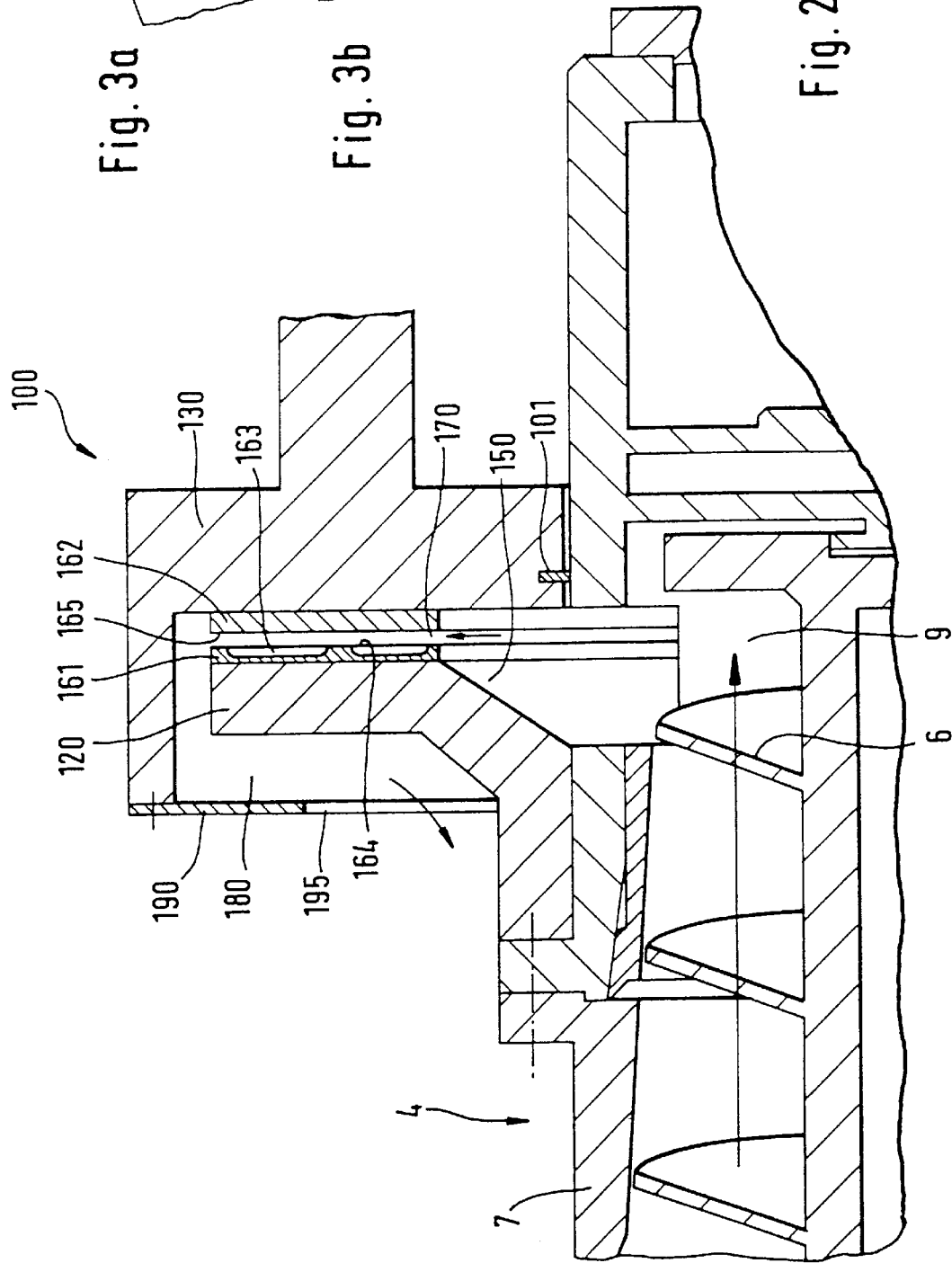

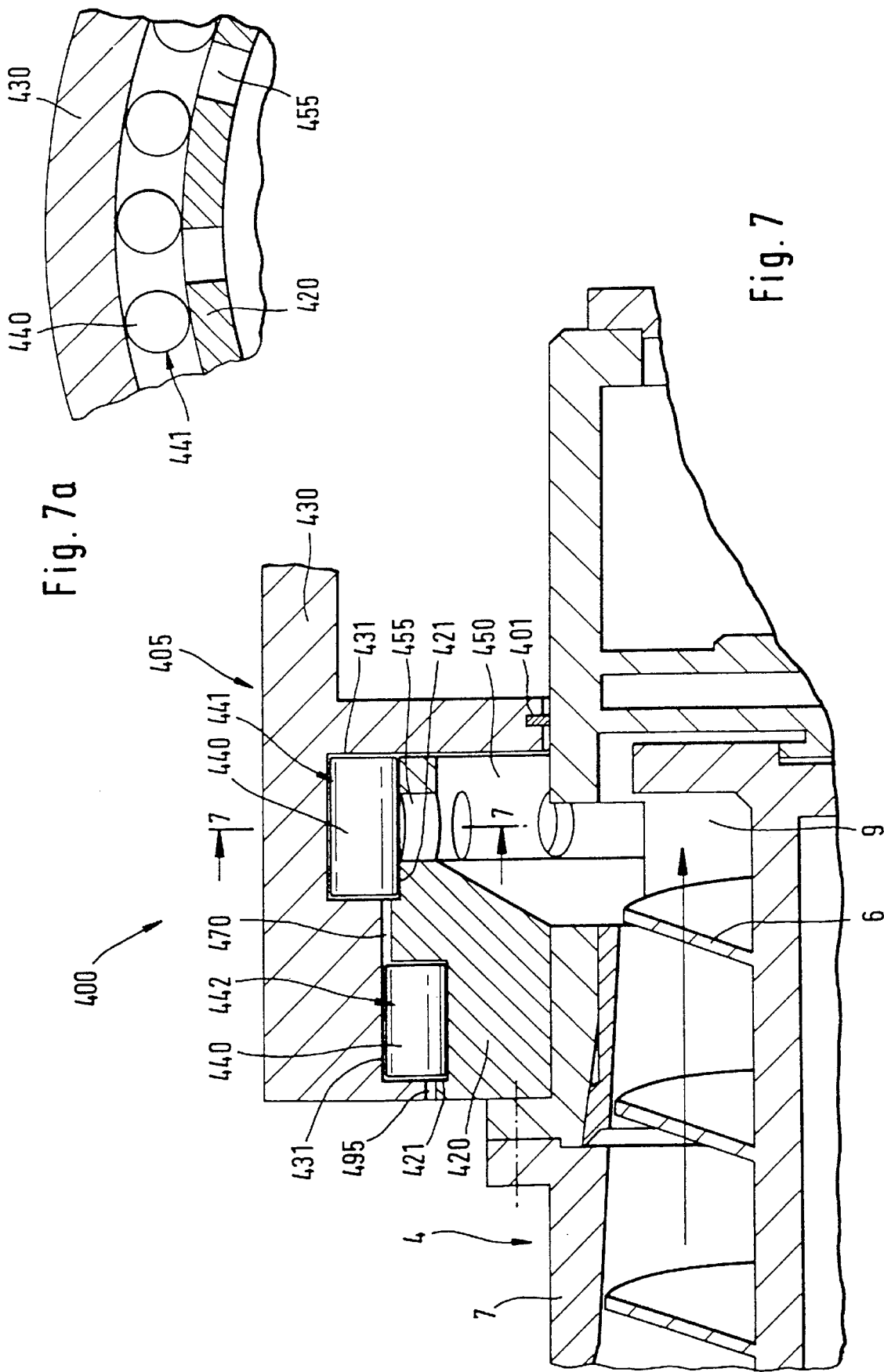

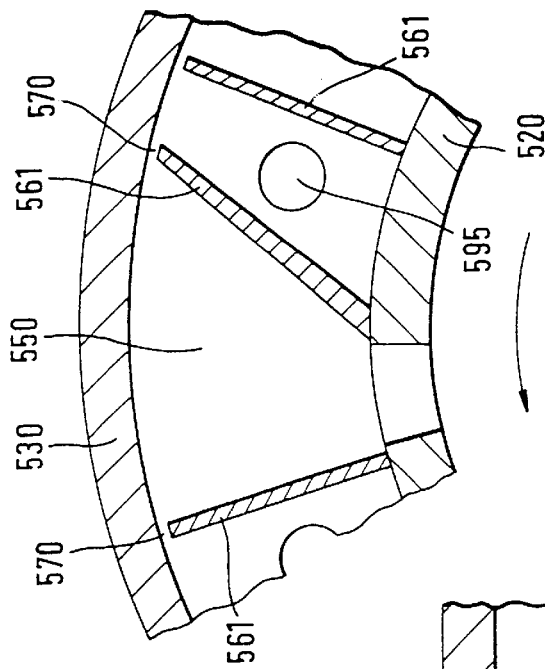
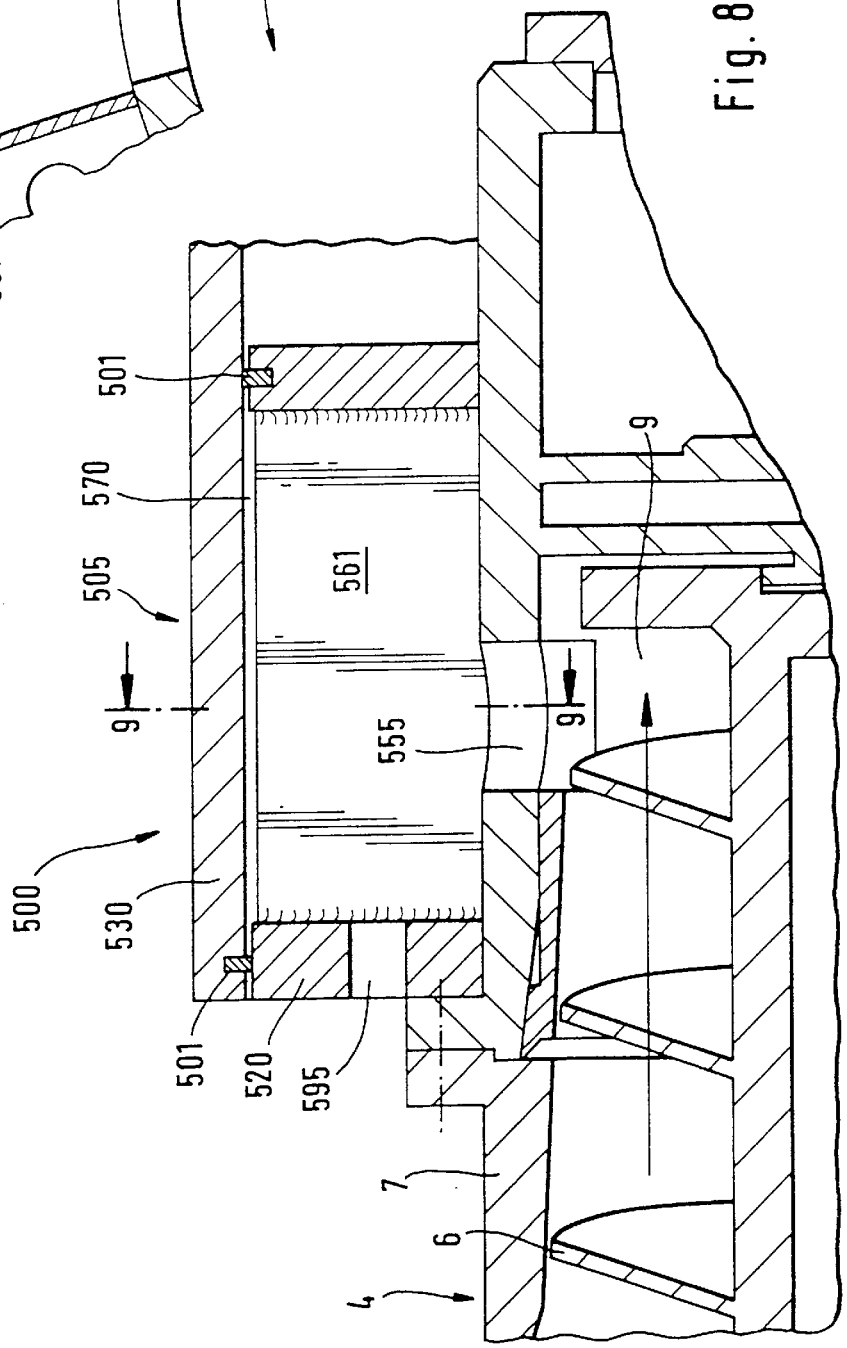
Fig. 9
Fig. 8

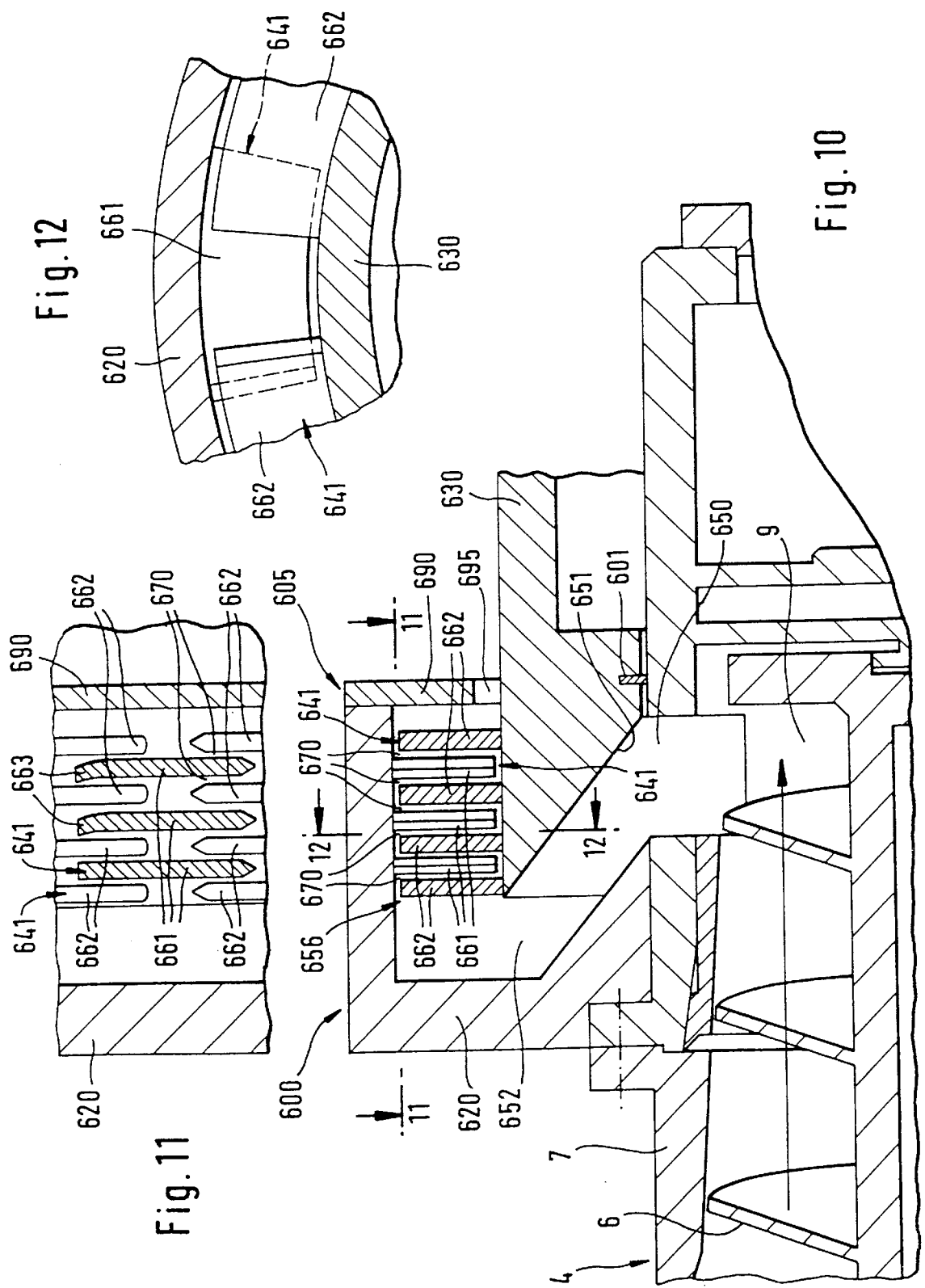

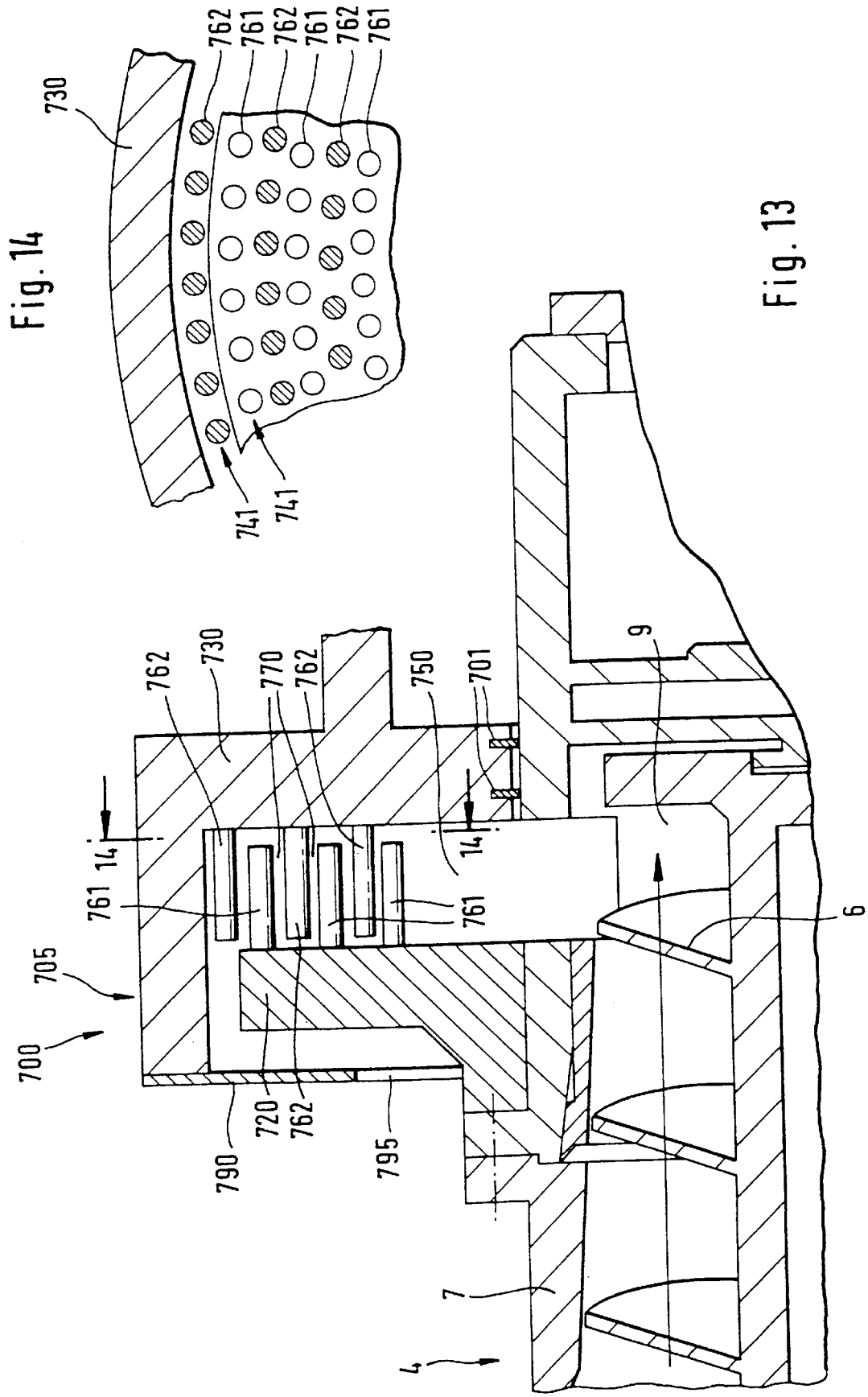

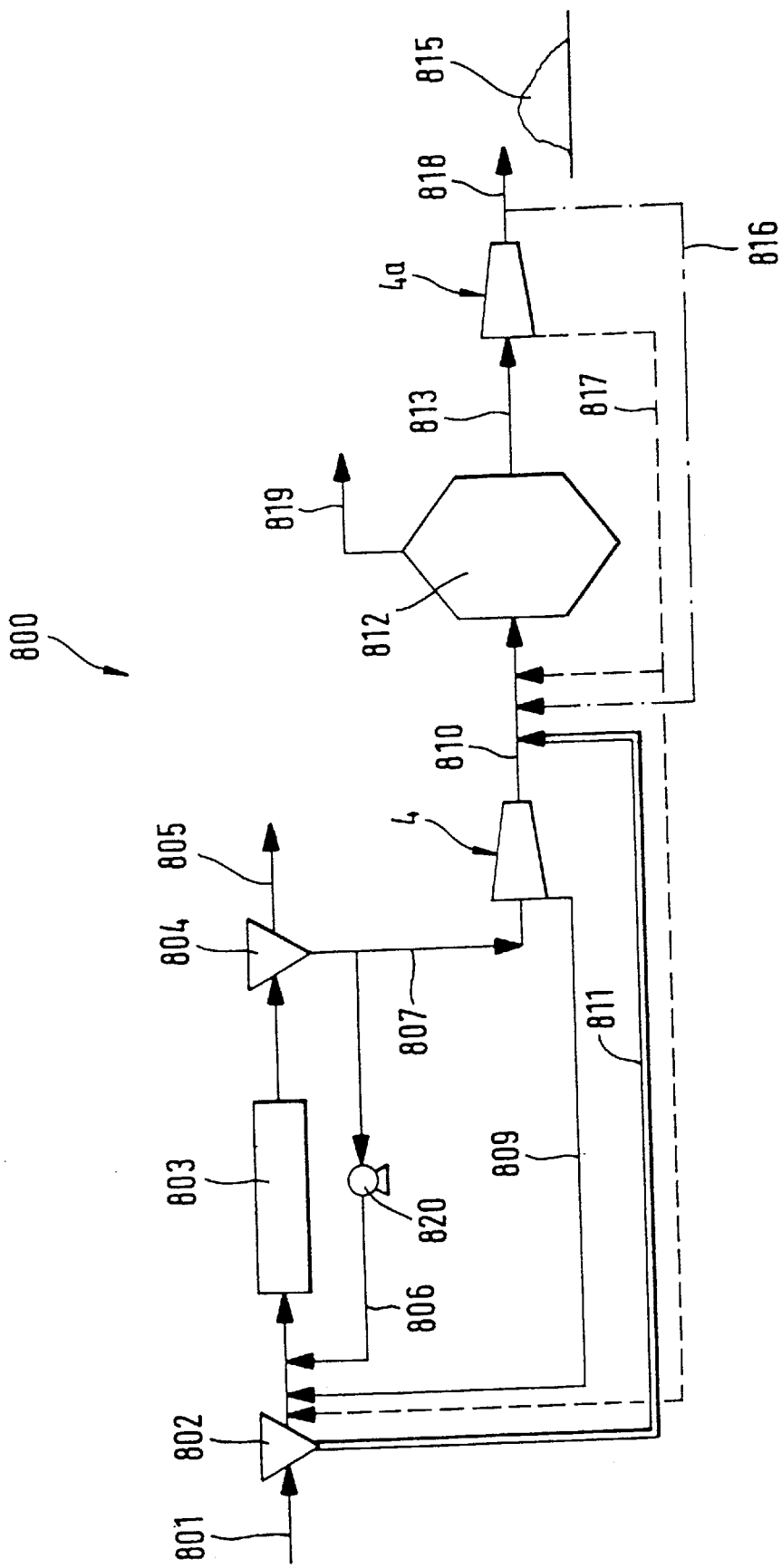

DEVICE AND PROCESS FOR THICKENING AND CONVEYING WASTE WATER SLUDGE

BACKGROUND OF THE INVENTION

1. Field of the Invention

The present invention concerns a device for thickening of waste water sludges, a sewage treatment or waste-water purification plant (hereafter waste-water treatment plant), a process for minimizing the amount of decomposed sludge or, as the case may be, the residual sludge in purification plants, as well as a device for treatment of waste water.

The inventive device as well as the inventive process serve to minimize or reduce the amount of sludge produced in purification plants, to improve dewatering, and to accelerate the bio-gas fermentation during an anaerobic methane fermentation of the sludge, the waste biomass, as well as during the anaerobic purification of waste water.

In the process of biological purification of waste a relatively large amount of sludge is produced, wherein the handling thereof and the economical use often leads to problems. In the aerobic biologic purification of the waste water at least two types of sludges are produced; primary sludge—that sludge which is produced by the primary sedimentation or settling of the introduced waste water and which experiences a rapid decomposition—and as the second sludge type the activated surplus sludge, which results after the step of the biological purification of the waste water. Herein primarily a mixture of microorganisms takes part, which are produced during the waste water purification and of which the count depends upon the of the number of the impurities removed as well as on the parameters of the process during purification. Both sludge types are processed in most waste-water treatment plants, above all the larger ones, by an anaerobic methane fermentation.

The anaerobic methane fermentation of organic substances is a process, in which a mixed culture of microorganisms stepwise decomposes a biologically decomposable organic mass under anaerobic conditions. The end products of this decomposition are methane, carbon dioxide, sulfur dioxide (Sulfan), nitrogen, hydrogen, the resulting biomass and a stabilized organic material (a residual which is not further decomposable).

Among the most important factors which influence the process of the anaerobic decomposition, there are included the composition of the substrate (which determines the specific production as well as the composition of the bio-gas), the presence of nutrients, the pH-value, the buffer capacity as well as the temperature. The economical feasibility of this process is dependent upon the dry substance concentration (solid substance concentration) of the material to be processed. For this reason the starting materials are frequently subjected to a thickening process, wherein this occurs either mechanically (centrifuge, press, among others) or with the aid of gravity.

For an optimal progress of the anaerobic decomposition the presence of a series of an organic nutrients is of consequence. The presence of a series of growth factors (reproductive factors) is important as well as vitamins and enzymes. For anaerobic decomposition, above all hydrolytic enzymes are of importance, which are capable of decomposing or reducing a large number of substances such as, for example, even solid and high molecular organic substances. Several of these materials can be synthesized by the microorganisms themselves, others must be added from outside the system.

2. Description of the Related Art

A laboratory or bench top possibility for simulating the bio-gas production during anaerobic methane fermentation of sludges, waste water, as well as other various organic materials is described in CZ-PS 242 979. The process disclosed in this patent is comprised therein, that the material to be fermented has added to it, or in given cases the anaerobic reactor has added directly to it, a stimulating material which is prepared separate from the laboratory waste water purification system and which is a mechanically or physically treated microorganism-containing biomass suspension of between 0.1 up to 10 weight-%, preferably 5 weight-%, depending upon the organic dry substance of the material to be processed.

In the lytic treatment (mechanical and physical disruption of cells) of the biomass suspension according to the state of the art the content of the cells of these microorganisms is partially set free.

The content of the microorganism cells or cells of other organisms which in the course of the destruction of cell walls and/or cell membranes are released into the solution (also called cell lysate), has a facilitating or stimulating effect upon the process of biological decomposition of the organic substances. The lysate of the cells occurs on the one hand in a natural way (autolysis) with deceased cells, on the other hand with the help of hydrolytic enzymes, which are released into the solution by fermentation bacteria, and further by the artificial decomposition or dissociation of microorganisms or organisms with the help of physico-chemical or mechanical methods.

The cell lysate stimulates on the one hand the function and the growth of microorganisms, on the other hand it contains a series of enzymes, which are directly necessary for the decomposition of organic substances. The lysate stimulates the functionality or operability of certain bacteria, which convert and/or release hydrogen and carbon dioxide, acetic acids, propionic acids, etc. Besides this it strengthens the decomposition of organic materials and increases the bio-gas production in anaerobic methane producing processes which has as a consequence a reduction of the total amount of the produced sludge as well as an increase in the bio-gas production. The cell lysate can likewise significantly influence the production of surplus activated sludge when using activation tanks.

The preparation of cell lysate in laboratory scale amounts according to the state of the art is expenfiltere in terms of the equipment necessary therefor as well as the required amount of energy. This is true for the hitherto known methods of cell decomposition or destruction such as, for example, in the disruption by means of mechanical methods (grinding, milling, pressing), sonification (ultra sound treatment), cavitation, repeated freezing and thawing, heating, among others.

The above described process according to the state of the art as described in CZ-PS 242 979 has above all the disadvantage, that it requires a separate preparation of the cell lysate -external of the actual purification or treatment device. As already mentioned above, this process is only suitable on a laboratory scale; a transition to an industrial scale process is not practicable for reasons of the large space requirement, the high energy cost and investiture cost and the additional personnel requirement. So it is, for example, neither economical nor technically useful to cyclically freeze and then thaw sludge in amounts which are measured in tons.

With the state of the art as described in CZ-PS 242 979 as a starting point, it is the task of the present invention to significantly reduce the sludge amount yielded under industrial scale conditions in a less expenfiltere and in a more economical manner.

SUMMARY OF THE INVENTION

The present invention provides a device for thickening and/or conveying waste water sludge, in particular surplus sludge. In its construction it is so designed that the cells of the organisms contained in the clarified sludge, in particular microorganisms, are at least partially lysed during the thickening.

By means of the inventive device the sludge produced in the purification plant is significantly reduced. Further, due to the fact that the cells of the microorganisms are lysed in the thickening device, it becomes possible to employ this device also in the realm of large scale.

As to industrial processing engineering, this occurs as already described in the German Patent Application 195 02 856.2 of the same applicant with the title "Device and Process for Reduction of Sludge Products in Purification Plants" of Jan. 30, 1995, the entirety of which is incorporated herein by reference. Reference is likewise made to the German Patent Application 195 27 784.8 of the same applicant entitled "Device for Thickening and Promoting of Waste Water Sludges" of Jul. 28, 1995, which is likewise completely incorporated herein by reference.

Thereby there is evolved a particular advantage, that the thickening apparatus can be employed to serve simultaneously for thickening and/or conveyance of sludge as well also for lysis of the cells, which makes the apparatus or the process economical. Beyond this there is in accordance with the inventive devices the possibility of continuous lysing of the cells at a relatively minimal sludge throughput, whereby it is avoided, that large sludge amounts must be processed at once.

Alternatively to the inventive thickening device in particular one with a centrifuge, which includes a lysing device, the cumulative various advantages of the invention can also be achieved also with a conveying device in particular a pump, which includes a lysing device. The lysing device therein is essentially similar in construction to the lysing device of the inventive assembly.

The purification plant according to the invention for waste waters comprises at least a settling tank with at least one effluent input; at least one conveyance device; at least one aerobic activation device; at least one thickening unit, which yields surplus sludge; and at least one anaerobic reactor and is thereby characterized, that the thickening device and/or conveyance device is so constructed, that the cells of the microorganisms contained in the surplus sludge are at least partially lysed during the thickening and/or conveyance.

Finally in accordance with the invention there is provided a process for reduction of sludge amounts or as the case may be residual sludge in purification plants, which comprises the following steps:

Allowing waste water to settle in at least one settling tank and conveying the settled or sedimented surplus sludge to least one anaerobic reactor by means of at least one conveyance device as well as further conveyance of the waste water into an aerobic activation unit or device;

aerobic conversion of the waste water after settling in at least one aerobic activation unit;

thickening of the surplus sludge in at least one thickening device or unit;

conversion of the surplus sludge in at least one anaerobic reactor; wherein the microorganisms contained in the surplus sludge from the thickening device and/or waste water are at least partially lysed in the thickening device and/or in the conveyance device prior to the decomposition tower.

By using the inventive device or the process according to the invention, the sludge production in treatment plants can be significantly reduced. As a result of the fact that the cells of the microorganisms are themselves lysed in the treatment device or, as the case may be, in the thickening and/or conveyance device, it is besides this possible, to utilize these devices or this process also in the large scale environment. Thereby an advantage is produced, that the thickening and/or conveyance device is simultaneously used for thickening and/or conveying the sludge as well also as for lysis of the cells, which makes the device or the process more economical. Beyond this it is possible in the device or, as the case may be, the process, to continuously lyse the cells with a relatively small sludge throughput, whereby it is avoided, that large sludge amounts must be simultaneously processed.

Since in the inventive device or, as the case may be, the inventive process, there is no longer any requirement for expenfiltere preparation of cell lysate outside of the purification plant, there are simultaneously achieved the advantages of no increased costs and no increased energy and personnel requirements. Besides this the efficiency or output of the anaerobic reactor is increased and the decomposition of organic substances is accelerated, problematic substances or compounds such as for example various xenobiotica or poison substances are more intensely decomposed, the production of combustible gas is increased and the energy balance sheet is improved as compared to the state of the art.

The above indicated disadvantages of the state of the art are overcome by the device according to the invention or, as the case may be, the purification plant according to the invention, wherein the treatment of sludge and waste biomass is accomplished by anaerobic methane fermentation as well as in the anaerobic waste water purification.

The present invention encompasses a device for thickening of waste water sludge with a centrifuge, wherein the centrifuge is provided with at least one lysing device for breaking open the cells of the organisms contained in the waste water sludge as well as a device for conveyance of sludge containing waste water with at least one such lysing device.

In the preferred embodiment of the present invention the lysing device is an integral component of the centrifuge or as the case may be the conveyance device, in particular a pump, and is preferably provided at the centrifuge exit side or, as the case may be, pump output side.

Of course a separate lysing device can however be provided on either the centrifuge input or, as the case may be, at the conveyance device input, as well as at the centrifuge output or, as the case may be, conveyance device output or in the conduit system independent of a direct constructional coupling with the centrifuge and/or the conveyance device.

The particular advantage of the present invention lies founded therein, that the present invention can be incorporated in the thickening devices according to the existing conventional waste water technology, in particular centrifuges or as the case may be conveyance devices, in particular pumps, whereby only a relatively small construction modification must occur, in order for them to meet the conditions of the present invention.

The device is essentially characterized therein, that it has a higher level of conveyancing and thickening effectiveness, when it includes a rotating conveyor screw as well as a rotating jacket, wherein the rotating jacket essentially provides a better conveyancing of the sludge and substantially prevents a coating or caking of the conveyer screw to the jacket of the centrifuge.

This effect is thereby strengthened, that the screw conveyor device and the jacket of the centrifuge rotate with different rotational speeds.

The rotational speed of the screw conveyor lies at approximately 10 RPM higher than the rotational speed of the centrifugal jacket.

The lysis device can, as already discussed above, be provided at the centrifuge input and/or centrifuge output and/or integrated in the centrifuge. This has the advantage, that hereby a variety of measures are made available, for adapting or fitting the present invention to the various conditions and constituencies and compositions of the waste water sludges in the various treatment plants.

In order to keep larger foreign bodies from the naturally relatively narrow entryway and passage spaces within the lysing device, it is frequently useful to provide a sieve device in the sludge introduction side for the lysing device. By this means the damaging of the lysing device by larger materials such as stones and non- decomposable waste materials is substantially prevented.

This type of filter device is preferably provided in such a manner, that it is easily changed out during the operation of the treatment plant and the centrifuge. Accordingly, there is for example envisioned the possibility of a bifurcated sludge input in the form of a bypass, wherein the sludge path can be conducted through the bypass with intact filter device, when the filter device of the other pathway must be cleansed. The lysing device itself can be constructed in a number of ways. Whichever specific lysing device is to be selected depends upon the respective sludge conditions, so that here a wide selection is available as to which centrifuges are to be combined with which lysing devices for which purpose.

Conveyance devices can be employed, which combine conventional pumps with a lysing device in accordance with the present invention.

At the present time experience has been had with seven different lysing devices.

So there is a lysing device constructed for example as a friction grinding unit, which means, that basically shearing and rubbing forces in the manner of a grinder using a mill stone is responsible for the lysing effect.

Such a friction grinding unit as lysing device is provided at the inventive device, wherein this friction grinding unit is comprised of at least one grinding disk, which serves for grinding of the sludge and the therein contained cells.

In such a device the sludge which has been de-watered by the centrifuge is preferably mechanically rubbed between two roughened surfaces, wherein due to the high shear force, which occur within the sludge and the cells between the rubbing surfaces, the cells of the microorganisms and higher organisms are ruptured and therewith lysed.

Preferably such a frictional grinding unit is constructed as lysing device, wherein a grinding disk is connected with the rotating jacket of the centrifuge and rotates along with this and moves against an additional stationary grinding disk. Herein the separation between the grinding disks is in the range of 0.5–5 mm.

A construction of this type of a lysing device has the advantage, that it is achieved with little sealing requirement, that the space between the two grinding disks is adjustable whereby the degree of lysing is adjustable, and that a lysing device of this type is also capable of being constructed to provide multiple stages, wherein varying surfaces of the grinding disks or as the case may be, varying spatial separations between the grinding disks of the individual stages can be made.

On the basis of the relatively small gap between the two grinding disks, it is worthwhile to take measures to retain larger foreign bodies within the sludge by a filter at the input or feeder side, in order to prevent damage to the lysing device.

An increasing of the shear forces, which impact upon the cells contained in the waste water, is particularly caused thereby, that the grinding disks have recesses on their grinding surfaces, in particular notches, wherein these notches have an angle of incidence or angle of attack with respect to the radial direction. Therein it is particularly preferred, that these recesses are provided in the rotating grinding disk, since thereby a kind of pumping effect as well as a formation of relatively large pressure gradients and therewith a increased shear and thereby necessarily a increased lysing effect is brought about.

When angles of attack of the recesses or as the case may be notches are oriented with respect to the radial direction of the outer surface of the grinding disk, preferably the rotating grinding disk, the pumping effect can be increased or weakened in accordance with the angles.

The provision of staggered adjacent lying rows of notches has the advantage, that the sheering effect and the associated lysing effect is further strengthened also by the production of turbulence.

The residence time of the sludge in this type of lysing device can also be controlled thereby, that a dam or gate can be provided at the sludge exit, of which the height controls the volume of sludge in the lysing device and therewith the residence time.

Hereby the lysing efficiency can be controlled according to requirements and varied or as the case may be manipulated or adjusted.

A further type of a inventive device has a lysing device, which is likewise designed as a friction grinding unit, however in place of a grinding disk, a milling cone is provided for grinding the sludge and the therein contained cells.

The lysing effect as produced herein is similar to the above described embodiment of the inventive device, namely, at the output of the centrifuge and/or conveyance device, the sludge enters likewise in the milling cone and is rubbed between the rotating external cone, which has at least one grinding surface, and a preferably stationary inner cone. A kinematic reversal is also possible. The rotating external cone as well also as the stationary internal cone can, as necessary, be provided with surface recesses and in particular notches, which are here preferably provided in the direction of the jacket line of the grinding cone or at a angle of attack thereto, wherein these recesses have the same lysing strengthening effect as the recesses on the grinding disk in the above described embodiment.

Particularly preferred is, in the illustrative embodiment of the present invention, which employs a grinding cone as lysing device, that the cleft between rotating outer cone and the stationary inner cone is in certain conditions during operation capable of being varied and adjusted via a stop or detent and springs.

The embodiment of the device according to the invention which employs a grinding cone as a lysing device has the advantage that it is simple to adjust and that it can yield to large foreign bodies as a result of the spring mounting of the inner cone.

The inventive device for thickening of waste water sludge is provided with a so-called shape or profile rasp as the lysing device. In this profile rasp there is provided a stationary outer hull and a rotating rasp surface which is connected with the rotating jacket of the centrifuge, whereby a narrow cleft exists between the stationary outer hull and the rasp surface.

Sludge, which enters through an opening between the rotating rasp surface into the cleft between outer hull and rasp surface, is forced to flow into this narrow spatial separation, whereby the great pressure causes such high sheer forces to be produced that the cell walls of bacteria and other microorganisms such as for example protozoa burst and therewith are lysed.

The rotating rasp surface can have on its upper surface recesses, in particular wave shaped recesses, which further serve to increase the sheer forces.

The rasp surfaces can be provided on both sides of their exit opening with varying pitches or inclinations in the direction of the outer casing or shell, whereby that respective part of the rasp surface, which is directed towards the closed end of the device is narrower than that respective part of the rasp surface which is directed towards the sludge output opening, whereby a pressure gradient in the direction of the sludge outlet results.

As a result of the pressure gradient there is, on the one hand, a conveyance effect in the direction of the sludge exit achieved and, on the other hand, the shear forces working on the microorganisms are again increased, whereby the lysing effect is overall strengthened.

The sludge supply side for the profile rasp is preferably provided centrally and exhibits a space between rubbing surface and outer shell of at least 1 mm to maximal 10 mm.

The construction of the lysing device as a profile rasp has overall the advantage, that practically no sealing problems occur, that it is simple to construct, that no metal rubbing occurs and that larger particles can be shunted away, so that in given cases a filter or filter device can be dispensed with.

Beyond this the construction height in an industrial construction can be kept low so that a relative space saving construction is made possible.

The mechanism of lysing is achieved primarily by squashing and rubbing and the thereby resulting sheer forces.

A further embodiment of the present device for thickening of waste water sludge or, as the case may be, conveying device is disclosed, namely, one such device, with which the lysing device is provided as a roller or cylinder press.

In this embodiment of the inventive device, rollers are rolled in the manner of a roller bearing element upon the inner wall of a stationary outer shell by a rotating part, in the internal part rotating direction. Here in practice a stationary outer cylinder is provided, which has recesses in which the rollers can move. Beyond this the rotating part, which is connected to the jacket of the centrifuge, is likewise provided with recesses, in which a different set of rollers is mounted and via which are rolled over the inside outer circumference of the outer shell in the inside circumference rotating direction.

When sludge enters from the centrifuge output into such a lysing device, it enters into the internal space of the rollers and is taken along therewith, is rolled over and thus squashed, wherein high sheer forces occur which are sufficient to lyse the cells of the organisms contained in the waste water, in particular microorganisms, and in particular to finely lyse these.

One roller set is comprised of at least ten rollers, wherein a total of at least two roller sets are preferred.

A device according to the invention with a roller crusher as lysing device provides a good squashing and lysing effect, wherein the construction height can be maintained relatively low.

For a lysing device of this type however a relatively high precision is required in the construction of the individual parts as well as a relatively high running quietness is demanded, since even small mineral particles can eat at the device, so that a filter is preferably provided in this lysing device prior to the centrifuge.

A device for thickening of waste water sludges or, as the case may be, a device for conveying of sludge containing waste waters, in which the lysing device is constructed as a so called passing or paddle blade drum.

A passing drum of this type is comprised of multiple passing elements, which rotate within a stationary outer shell with a preferably adjustable spacing with respect to the inner wall of the outer shell. If sludge from the centrifugal input is supplied between the individual passing elements, then it is squashed by the narrow space between the outer shell and the individual passing elements which can be constructed for example as passing disks or blades, and the microorganism cells are disrupted by the thereby resulting high sheer forces.

The advantage of this type of lysing device lies founded therein that a very small construction space is possible and that multiple lysing devices of this type can be coupled one after the other in order to increase the lysing effect, preferably step-wise.

Since in the construction of the lysing device of this type however large foreign bodies can lead to damage to the passing elements, it is worthwhile to use a filter to remove larger foreign bodies prior to the centrifuge.

A device for thickening of waste water sludge or, as the case may be, conveying is addressed, which comprises a cutting unit as lysing device.

A cutting unit of this type is comprised of rotating rows of cutting elements, in particular knife rows, stationary cutting elements, in particular knife rows, as well as a dam at the sludge outlet of the lysing device, and the cutting elements are provided such that they interdigitate with each other without however contacting each other.

As a rule the sludge from the centrifuge output enters into the inner workings of the cutting device wherein the sludge leaves the centrifuge at approximately 50 m/s and then first impacts upon an inclined or canted surface, whereby already a portion of the cells are disrupted as a result of the impact impulse. The sludge is further conveyed via a canal or channel in the cutting unit where it is pressed through and subject to a multiplicity of rotating knives on the one hand and stationary knives on the other hand perpendicular to a rotation plane, and the sludge is subjected to enormous shredding and shearing forces by the cutting elements which are preferably constructed as knives, whereby the cells, which are contained in the waste water sludge, are lysed. The primary physical manner of operation lies thereby in the cutting and impacting of the cells.

The distance between the rotating and the stationary knife rows may be adjustable, whereby the lysing effect of the cutting unit and the characteristics of the sludge can be accommodated.

In practice it has been determined, that the knives rotate with a speed of approximately 50–100 m/s, preferably 80 m/s.

This speed ensures on the one hand a sufficient lysing effect and on the other hand a relatively high surface life or edge life of the cutting elements.

The knife rows are preferably so staggered that adjacent lying knife rows are so positioned, that regions in which one knife row is interrupted, there is no interruption in the adjacent knife row, whereby the lysing effect is significantly strengthened.

A further possibility for increasing the lysing effect lies therein, that the ends of the cutting elements, in particular, the knife ends, have a blade angle or an angle of attack to the rotation direction of the cutting unit, so that hereby a part of the sludge is again directed to the previous cutting element row, in particular knife row, so that essentially a pumping effect in the direction of the centrifuge results and hereby the residence time of the sludge within the cutting unit if desired can be drastically increased.

The residence time is likewise adjustable by the height of the gate or dam at the sludge outlet.

The advantage of constructing the lysing device of the inventive device as a cutting unit lies founded therein, that this type of lysing device can be constructed for improving the level of effectiveness of the lysing of the cells of the microorganisms, for example by increasing the number of knives or by changing the angle of attack of the knives, so that an excellent mincing occurs and the residence time is adjustable by multiple construction parameters, such as for example, dam or gate height, angle of attack of the knives as well as separation between rotating and fixed or stationary cutting elements, length of the cutting elements in the direction of rotation and height of the knives.

Since the knives as cutting elements are relatively sensitive, it is preferred that filtering occur for filtering out of larger foreign bodies, preferably already at the centrifuge inlet or in cases at the entrance of the conveyance device.

In order to increase the life of the cutting elements, it is preferred that hard materials are employed therefore, such as for example chrome-vanadium-molybdenum-alloys or titanium, as well as tungsten carbide or diamond powder containing cutters.

The device according to the invention encompasses a pin disk mill or grinder as the lysing device.

Fundamentally, a pin disk grinder of this type is constructed similar to the cutting unit, however with the difference that no cutting elements but rather pins are provided on the rotating and the stationary parts, wherein these pins which are arranged in the form of pin rows engage in one another and wherein the rotating pin rows do not contact with the stationary pin rows.

In this type of lysing device the sludge emitted from the centrifuge output or, as the case may be, at the output of the conveyance device enters into the inside of the pin mill unit, wherein the sludge is forced through the narrow gaps of the interdigitating and partially rotating pins, whereby the cells contained in the sludge are lysed by being impacted and smashed. Beyond this, high sheer forces occur between the individual pins, whereby likewise the lysis of cells occurs.

The spacing between the stationary and rotating pin rows is adjustable, whereby the degree of lysing can be adjusted.

The pins rotate with a speed of approximately 50–100 m/s, preferably approximately 80 m/s.

Adjacent lying rows of pins are oriented to be staggered so that in areas in which no pins are provided in a pin row the adjacent pin row is provided with pins. The pins may be provided at an angle to the axis of rotation. Thereby likewise an increase in the lysing effect can be achieved.

The height of the dam at the sludge outlet can be adjusted or varied in the lysing device of this type whereby again the residence time of the sludge within the lysing device can be adjusted to meet the requirements.

An inventive device for thickening of waste water sludge or, as the case may be, for conveying of sludge containing waste water, with a lysing device which is constructed as a pin milling or grinding unit has the advantages, that the residence time is adjustable, that it can be constructed in a variety of arbitrary manners and that the effect is very easy to vary for example by altering the number of impacting pins, and that impacting pins are easily changed out as necessary.

It is desirable also in this embodiment that foreign bodies be retained by a filter or filter device preferably at the centrifuge or, as the case may be, pump inlet.

A purification plant is addressed which includes at least one settling tank with at least one affluent (inlet) as well as at least one conveyance device, at least on aerobic activation device and at least one anaerobic reactor, wherein the purification plant includes at least one device for thickening of waste water sludge, in which a lysing device is provided.

As lysing device one can employ, besides those already described, also a vacuum device and/or pressurization device, in particular a press device and/or grinding device and/or acoustic irradiation device, preferably an ultrasonic device and/or vibration device. By these various possibilities the plant can be adjusted to optimized to fit the requirements of the respective waste water and/or sludge. Further the lysing effect can be strengthened or weakened according to requirements, whereby the device according to the invention or, as the case may be, the therewith carried out process, is very adaptable.

The purification may include a supplemental settling or clarification tank between the aerobic activation device and the thickening device in order to improve the purification or clarification. Further the supplemental clarification tank can also assume the function of a storage unit or act as a buffer.

The aerobic activation unit is preferably connected directly to the settling tank, which has the advantage of a unitary conveyance system and a reduced odor capacity.

The conveyance device or, as the case may be, conveyance unit can for example be a return sludge pump, which is preferably situated downstream of the supplemental clarification tank and is connected with an input of the aerobic activation device. Therewith the aerobic treatment of the waste water can be further improved. Further the conveyance device can for example be a paddle wheel device. Also, the conveyance device for conveying the thickened sludge to the anaerobic treatment can be provided with a lysing device.

Preferably the thickening device of the treatment plant is a centrifuge with a suitable lysing device. This has the advantage, that besides the lysing of cells a substantial de-watering of the sludge can be accomplished. Therewith simultaneously the potential transport costs of sludge can be reduced. A further advantage also lies therein, that the water content of the sludge can be adjusted.

Further, a thickening and/or de-watering device, preferably a centrifuge, can be provided also after the anaerobic reactor, in order that the sludge is dried as intensely as possible prior to the final storage and/or burning. Here also there results the above described advantages of reduced transport costs as well as adjustability of water content.

In accordance with the invention at least one device for thickening of waste water sludge with a lysing device is employed in the treatment plant.

The lysing device can thus for example be a friction grinding unit, in particular, a grinding disk for grinding or a milling cone grinding unit, a profile rasp, a roller crusher, a passing drum, a cutting unit or a pin milling unit.

Of course, also combinations of these lysing unit types can be considered in one and the same centrifuge and/or thickening device and/or conveyance device or conveyance unit.

Beyond this the purification plant in accordance with the invention can be employed with multiple centrifuges and/or conveyance devices with respectively various lysing devices. The advantage hereof lies founded therein that the adjustment or the coordination of the lysing device can by such measures be coordinated to the sludge consistency and composition.

The aerobic converted waste water can be supplementally clarified in at least one supplemental clarification tank or reservoir and the purified waste water can be conveyed off and at least a part of the settled clarification sludge can be further conveyed to a thickening device. This has the advantage, that less volume must be further processed, whereby the facility is made more economical.

The anaerobic converted sludge can also be thickened in a further thickening device (centrifuge). The cumulative centrate is, after the centrifuge, conveyed to the aerobic activation device. A part of the centrate of the centrifuge can be conveyed to the aerobic reactor for stimulation.

Preferably an amount of approximately 0.5–50% of the amount of the originally present organism cells are lysed. Therewith the stimulation and/or the resulting sludge amount can be controlled.

Also a portion of the anaerobic converted and/or thickened sludge can be returned back to the anaerobic reactor, in order that it be further decomposed.

For decomposition (destruction) or as the case may be lysis of a portion of the cells there can for example be used the centrifugal force acting upon the cells during pumping and/or the centrifugation of the material being processed (activated or anaerobic stabilized sludge or, as the case may be, another biomass).

A further advantage of the process carried out with the purification or treatment plant according to the invention is that the anaerobic reactor produces a combustible gas, in particular methane. The combustible gas produced in the process can be used for production of electricity, wherein the produced electricity is preferably employed directly for powering the clarification plant and/or feeding directly to an electrical network.

Further advantages and characteristics of the present invention come to light on the basis of the description of illustrative embodiments as well as through the figures.

BRIEF DESCRIPTION OF THE DRAWINGS

FIG. 1 an overview of an inventive device in longitudinal section.

FIG. 2 a sectional view of a part of the inventive device with a friction grinding unit lysing device according to a first embodiment.

FIG. 3*a* a schematic representation of the outer surface of a grinding or milling disk, which is utilized in the inventive device according to the first embodiment;

FIG. 3*b* a schematic representation of the outer surface recesses according to FIG. 3*a* in an alternative design;

FIG. 7 a sectional view of a part of the inventive device according to a fourth embodiment;

FIG. 7*a* a side section along the line 7—7 in FIG. 7;

FIG. 8 a sectional view of a part of the inventive device according to a fifth embodiment;

FIG. 9 a section view along the line 9—9 in FIG. 8;

FIG. 10 a sectional view of a part of the inventive device according to a sixth embodiment;

FIG. 11 a sectional view along the line 11—11 in FIG. 10;

FIG. 12 a sectional view along the line 12—12 in FIG. 10;

FIG. 13 a sectional view of a part of the inventive device according to a seventh embodiment;

FIG. 14 a sectional view along the line 14—14 in FIG. 13; and

FIG. 15 a schematic representation of the embodiment of the inventive treatment plant.

DETAILED DESCRIPTION OF THE INVENTION

Figure 4:
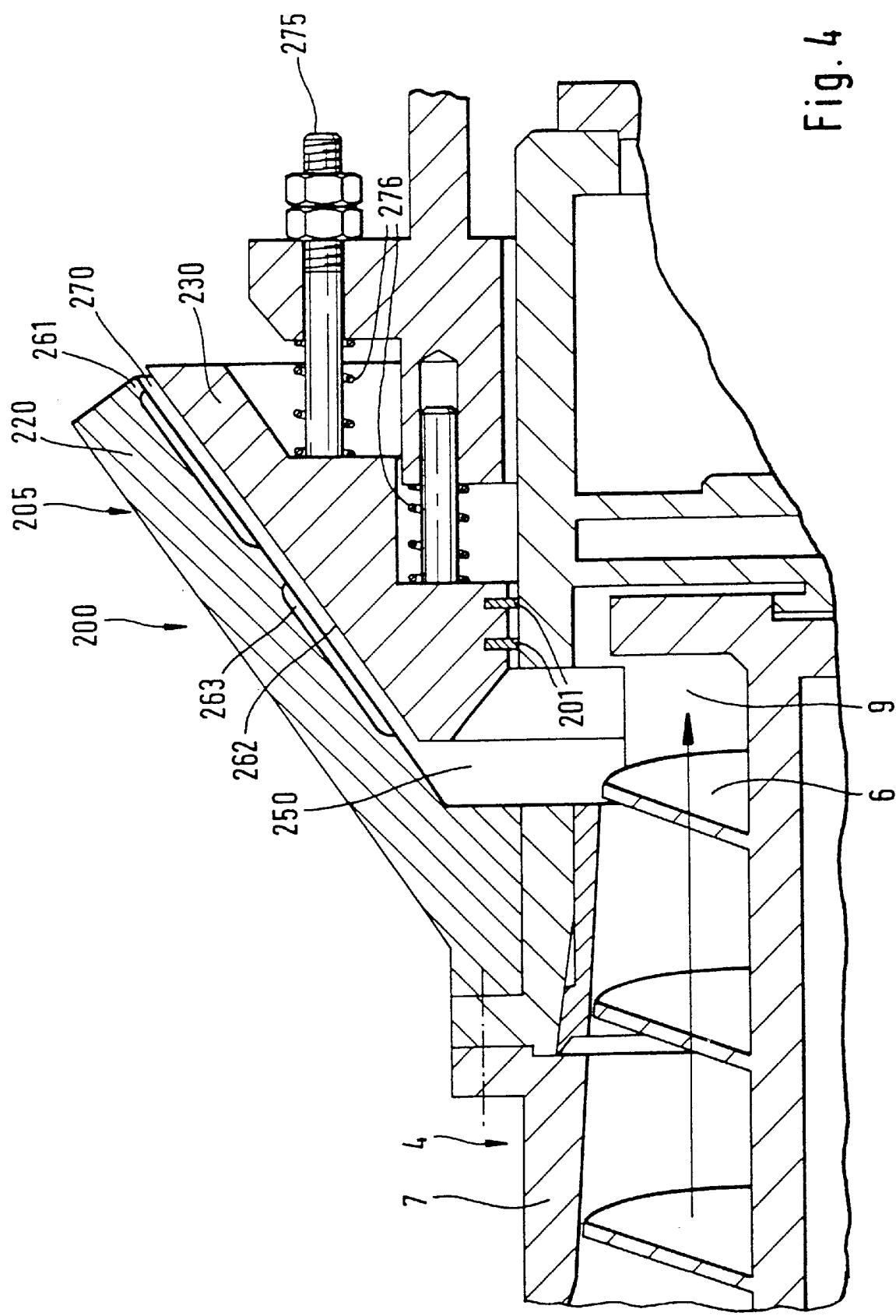
FIG. 4 a sectional view of a part of the inventive device according to a second embodiment.

In the following the inventive device is described by reference to a centrifuge with a lysing device. The invention is however is not limited thereto; rather, any suitable conveyance device for sludge containing waste water can be combined with the described lysing device and be employed at various positions within a treatment plant in the sense of the present invention.

In FIG. 1 the device for thickening of waste water sludge is indicated with 1. The device 1 is comprised of a housing 2, on the inside 3 of which a centrifuge 4 is provided. The centrifuge 4 has on the inside 5 thereof a snake or screw conveyor 6 as rotating conveyance device as well as a rotating jacket 7.

In the thickening of the waste water sludge the treated sludge is conducted via a not shown tube or conduit to a centrifuge entryway 8 of the centrifuge 4. The waste water sludge is then conveyed through the rotating screw conveyor 6 in the inside 5 of the centrifuge 4 in the direction of the arrow indicated in FIG. 1 to the back end 9 and finally to the centrifuge exit. In given cases the screw conveyor 6 rotates with a circumference speed of approximately 3010 RPM and the jacket 7 rotates with a circumference speed of approximately 3000 RPM, wherein the rotational direction of the screw conveyor 6 and the jacket 7 are identical.

At the back end 9 of the centrifuge 4 there is provided, for example, a lysing device 10 within the housing 11.

The lysing device 10 includes a rotating part 12 as well as a stationary part 13. The rotating part 12 of the lysing device 10 as well as the jacket 7 of the centrifuge 4 are driven via a drive 14.

The screw conveyor 6 and the centrifuge 4 are driven via a second drive, not shown in FIG. 1, for example, a hydraulic drive or via a drive gear.

For obtaining lysate containing sludge, the processed sludge, which is conventionally available in treatment plants, is conveyed via a screw conveyor 6 of the centrifuge 4 to a centrifuge exit 9, in order to have access to the inner 15 of the lysate device 10. Cells of organisms, in particular microorganisms, such as protozoa and bacteria, as well as algae and nematodes, as well as components of higher plants, are destroyed or disrupted in the lysing device 10 or, as the case may be, are lysed, so that their membrane and/or cellular wall is ruptured and the cellular content is released to the surroundings.

Since naturally not all of the cells present in the sludge are lysed, the cell content of the lysed cells serves as a nutrient for other organisms during the treatment technological further processing of the sludge, whereby on the one hand the bio-gas production, in particular methane production, in the decomposition tower is increased substantially, and wherein conversion of the total sludge mass is reduced dramatically.

In the following there will now be described embodiments of the inventive device with varying lysing devices 10.

FIG. 2 shows a lysing device 100, which is provided to the centrifuge output 9 of the centrifuge 4 of a device 1 for thickening of waste water sludges.

The rotating part 120 of the lysing device 100 according to FIG. 2 is connected with the jacket 7 of the centrifuge 4, so that it rotates with the jacket 7. The stationary part 130 of the lysing device 100 is constructed as a stationary cup. In the embodiment according to FIG. 2 the lysing device 100 exhibits as a friction grinding device on a part of the outer surface of the rotating part 120 a grinding or milling disk 161. The stationary part 130 of the lysing device 100 likewise exhibits a milling disk 162.

In this exemplary case the milling disk 161 exhibits recesses 163 which are preferably oriented in the radial direction according to FIG. 3a. As a result of the rotation of the screw conveyor 6 and the jacket 7 of the centrifuge 4 the waste water sludge is conveyed in the direction shown in the arrow to the centrifuge exit 9 and transported with a speed of approximately 50 m/s into the inside 150 of the lysing device 100. The sludge must now pass through the cleft 170 where it is ground between the milling surfaces 164 and 165. Thereby the recesses 163, which are preferably provided in the rotating milling disk 161, are of particular advantage since they enhance the milling and sheer forces of the lysing device 100 and therewith lead to a increased cell lysing.

After the sludge has been ground in cleft 170, it collects as a result of the centrifugal force in the upper end 180 of the lysing device 100 shown in FIG. 2. The sludge height and therewith the cumulative residence time of the sludge in the lysing device 100 is determined on the one hand by the breadth of the cleft 170, which in this example is approximately 2 mm, as well as the height of the dam 190.

After the passage through the lysing device 100 the sludge exits in thickened form at the exit 195 of the lysing device 100.

According to FIGS. 3a and 3b the recesses 163 on the upper surface of the rotating grinding disk 161 are preferably constructed or designed as notches in a radial direction, but can however, according to FIG. 3b also exhibit an angle of attack with respect to the radial direction.

In the example case it is particularly preferred, that the recesses 163 are arranged to be staggered. This means, that adjacent lying notch rows 141 are so arranged, that in regions in which the notch row 141 is interrupted, the adjacent notch row 141 does not exhibit any interruption.

The advantage lies on the one hand in an elevated pumping effect and a development of greater pressure gradient within the cleft 170, so that overall a noticeably increased lysing effect of the lysing device 100 results.

In any case the lysing device according to FIG. 2 can include multiple lysing devices 100, so that a multi-step lysing device is provided, whereby the lysing effect is yet further significantly increased.

Of course the number of lysing device steps is limited by the necessary energy expenditure and the relationship to the bio-gas production, that is to say, with other words, the energy requirement/notch-relationship.

Beyond this a sieve or filter step can be provided for retaining the larger foreign bodies, which in certain cases could damage the lysing device 100, prior to entry of the sludge in the cleft 170 or also prior to the centrifuge entrance 8.

In FIG. 4 the lysing device 200 of the inventive device 1 is shown in a second embodiment. The lysing device 200 is in this case constructed as a friction grinding unit, and more specifically as a milling cone 205. The rotating outer cone 220 of the milling cone 200 is connected with the jacket 7 of the centrifuge 4. The grinding or milling surface 261 of the outer cone 220 is provided with recesses 263. In the case of the example such recesses 263 are preferred, which are directed in the direction of the jacket line of the milling cone 205. Fundamentally it is however also possible, that the recesses 263 are provided at an angle of attack to the jacket line of the milling cone 205. In exemplary cases the recesses 263 are constructed as notches on the milling surface 261 of the outer cone 220 in such a manner, that adjacent lying notch rows are provided to be staggered, so that regions in which the notch rows are interrupted, the adjacent notch row does not exhibit an interruption.

Hereby similarly a better lysing effect is achieved.

Opposite to the rotating outer cone 220 lies a stationary inner cone 230, which exhibits a milling surface 262. Between the inner cone 230 and the outer cone 220 of the lysing device 200 there is a cleft 270, of which the breadth can be changed via an adjustment device 275.

Figure 5:
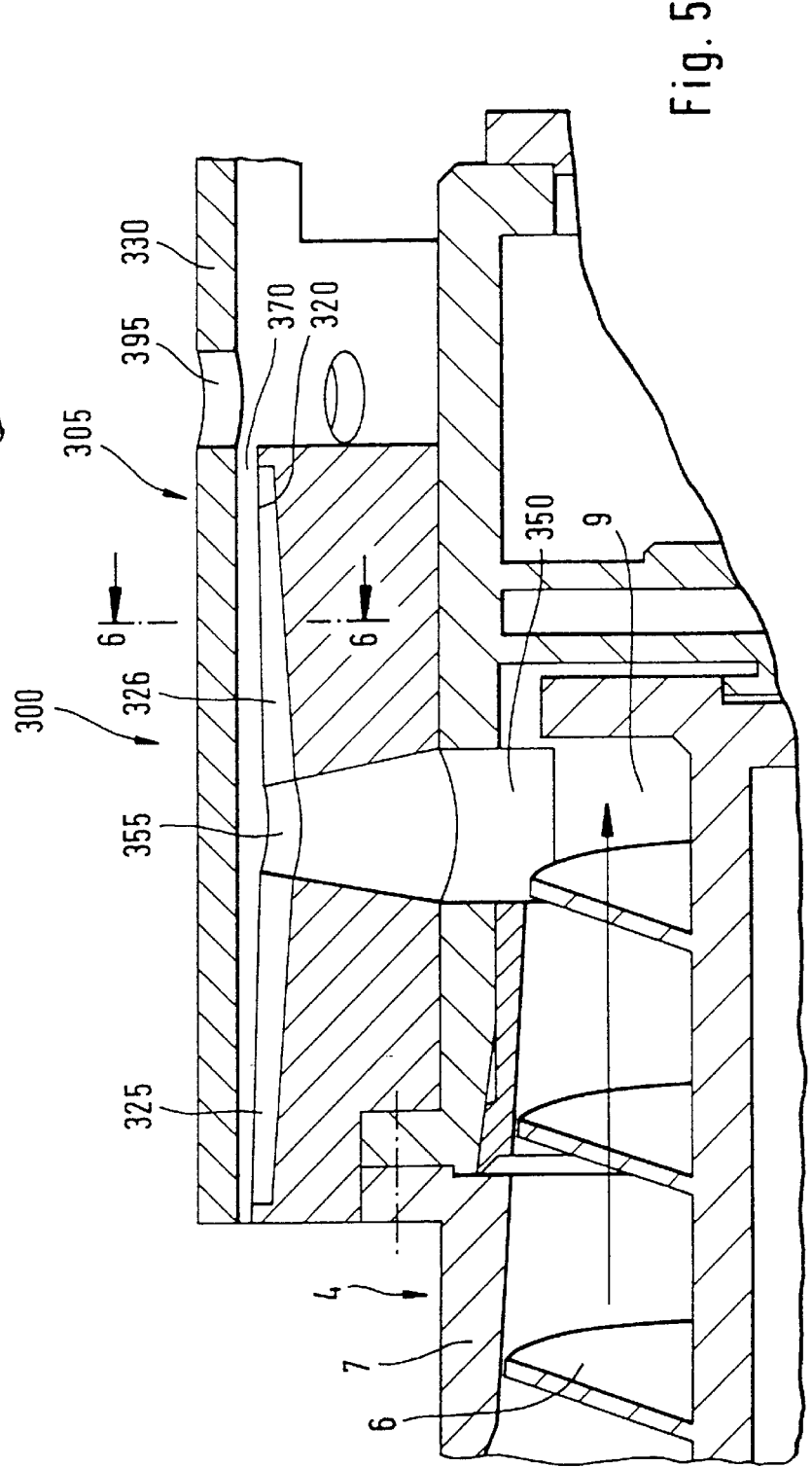
FIG. 5 a sectional view of a part of the inventive device according to a third embodiment.

For improving the pumping effect and for the improved distribution of the sludge the depth of the recesses 263 are so selected in the case of the example that they correspond approximately with the breadth of the recesses 263. Particularly advantageous on a milling cone 205 as a lysing device 220 of a device 1 for thickening of waste water sludge lies based therein, that with a lysing device 200 of this type in the form of a milling cone 205, foreign bodies in the sludge which enter into the inside 250 of the milling cone 205 do not result in disruption of the milling cone 205, but rather on the basis of a spring mounting 276 can be received, so that a removal of foreign bodies by means of a sieve or filter is not absolutely necessary. FIG. 5 shows as a lysing device 300 a profile rasp 305 as third illustrative embodiment of the device 1 of the present invention. The profile rasp 305 is comprised of a rotating rasp surface 320 and a stationary outer shell 330. The rotating rasp surface 320 is connected with the jacket 7 of the centrifuge 4. According to FIG. 5 the sludge is conveyed in the direction indicated by the arrow through the screw gear or screw conveyor 6 as well as the rotating jacket 7 into the inside 350 of the profile rasp 305 and passes out an exit opening 355 in the cleft 370 between the rotating rasp surface 320 and the stationary rasp surface 330 and is there squashed and milled, so that the cells contained in the sludge are lysed in the cleft 370 as a result of the high shear forces and the high pressure within the cleft 370, whereby their cellular content is released into the surrounding medium.

For increasing the pressure within the cleft 370, in this example the part 325 of the rotating milling surface 320 farthest away from the exit 395 is inclined more strongly toward the outer jacket 330 and the part 326 of the rotating milling surface 320 closest to the exit 395 is less strongly inclined towards the stationary milling surface 330 so that in this area a broader cleft 370 results than on the other side from the exit opening 355. This plane or elevation which increases towards the outside produces a significant pressure increase which has the effect of increasing the lysing effect of the lysing device 300.

In this embodiment it is preferable, so that practically no sealing problems occur, to construct the embodiment of the lysing device in a simple manner, so that no metal rubbing occurs and that larger particles can be diverted sidewards, so that as a rule no additional filtering means are necessary.

Figure 6:
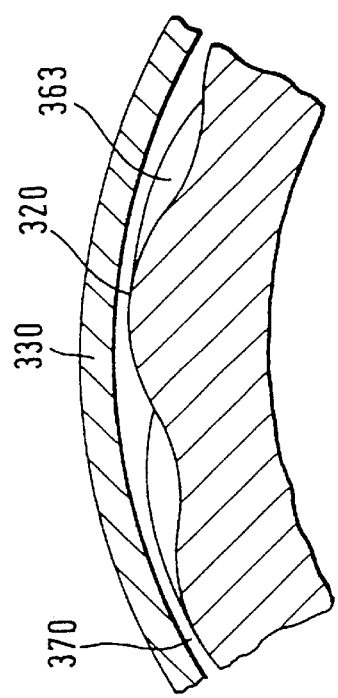
FIG. 6 a sectional view according to the section 6—6 in FIG. 5.

FIG. 6 shows a section along line 6—6 in FIG. 5. According to this embodiment of the lysing device 300 the profile mill 305 (sic) exhibits on its rotating rubbing surface 320 wave shaped recesses 363, which preferably exhibit an angle of attack to the rotation of direction. In an exemplary case the breadth of the cleft 370 in its narrowest point is approximately 2 mm and its broadest point is approximately 10 mm.

In accordance with this embodiment the sludge is forced to flow through the narrow space between the stationary milling surface 330 and the rotating rasp surface 320, which exhibits wave shaped recesses 320. Thereby a higher pressure results in the cleft 370 which causes such a high shearing force to result, that membrane and cell walls of the microorganisms, in particular bacteria, are shredded and release their cytoplasm into the surrounding medium.

FIG. 7 shows as lysing device 400 a roller crusher 405 as a fourth embodiment of the present invention.

The rotating part 420 of the roller crusher 405 is connected with the jacket 7 of the centrifuge 4, so that it rotates along with it. The lysing device 400 is closed off towards the outside with a stationary part 430, but however exhibits an outlet opening 495 between the rotating part 420 and the stationary part 430.

Both the rotating part 420 as well as the stationary part 430 exhibit openings 421 and 431. In the openings 421 and 431 roller bodies, in this example rollers 440, are provided. In exemplary cases the lysing device 400 exhibits two roller sets 441 and 442.

During rotation of the rotating part 420 of the roller crusher 405 the rollers 440 move in the manner of a roller bearing between the rotating part 420 and the stationary part 430.

As a result of the movement of the jacket 7 and the screw conveyor 6 in the direction indicated by the arrow according to FIG. 7, the sludge enters from the centrifuge exit 9 of the centrifuge 4 into the inside 450 of the roller crusher 405 as lysing device 400. The organism-containing purified sludge then passes through the exit opening 455 between the rollers 440, so that the rollers 440 when in motion engage the sludge between each other, roller over and thereby squash it in such manner that the cells contained in the sludge are lysed.

The sludge which has been squashed and lysed in this manner is then conveyed via cleft 470 to the next roller set 442, where it is newly roller over and squashed by the orbiting rollers 440, so that even more organismic cells are disrupted, so that their cellular content is released to the environment.

The sludge processed with the roller crusher 405 finally leaves the lysing device 400 via its outlet opening 495 where the sludge then, according to need, is further processed.

A particular advantage of the present exemplary fourth embodiment of the device 1 for thickening of waste water sludge according to FIG. 7 is founded therein, that various cleft gaps 470 can be employed and various roller sizes can be utilized depending upon the lysing effect to be obtained, so that by varying the parameters the breadth of the cleft 470, the size of the rollers 440, and the number of the roller sets 441, 442, a precise adjustment of the lysing amount can be achieved.

It is of course also possible, to provide not shown recesses in the upper surfaces of the rollers 440, which can be provided both radially, as well also in the direction of the jacket line of the roller cylinder, and as well also with an angle of attack to the direction of rotation.

In FIG. 7a a sectional view along line 7—7 in FIG. 7 is shown through a first roller set 441 and the exit opening 455.

In FIG. 8 there is shown as a lysing device 500 a passing drum 505 according to a fifth embodiment of the present invention.

The passing drum 505 comprises a rotating part 520 and a stationary part 530, which are sealed with respect to each other via seals 501.

On the inside 550 of the lysing device 500 there are provided passing elements 561, in exemplary cases in varying angles to each other.

As in the other embodiments the rotating part 520 is connected with the jacket 7 of the centrifuge 4.

As a result of the movement of the screw conveyor 6 as well as the jacket 7, the sludge is conveyed to the centrifuge exit 9 in the direction shown in the arrow and it passes then through the exit opening 555 into the inside 550 of the passing drum 505. Sludge and the therein contained microorganisms, such as for example bacteria, are then squeezed through the narrow cleft 570 between the stationary part 530 and the passing elements 561, whereby high shear forces result, so that bacteria and other microorganisms are shredded by this shear force and are thereby lysed, whereby their cellular content is released to the surrounding medium.

The sludge processed in the lysing device 500 exits at the exit opening 595 and can in suitable manner be further processed. FIG. 9 shows a section through the passing drum 505 according to line 9—9 in FIG. 8.

FIG. 10 shows as lysing device 600 a cutting unit 605 as sixth embodiment of the present device 1 for thickening of waste water sludge. The cutting unit 605 includes a rotating part 620 which is provided with cutting elements 661.

The rotating part 620 is connected with the jacket 7 of the centrifuge 4. The stationary part 620 of the lysing device 600 includes cutting elements 662, which fit within the cutting element 661. In the exemplary case the cutting elements are provided as knives, wherein the knives are arranged both side-by-side as well as one behind the other, wherein preferably an arrangement according to FIG. 12, which shows a section along line 12—12 in FIG. 10, are provided in standard arrangement.

The rotation of the rotating part 620 of the cutting unit 605 occurs in such a manner, that the individual cutting elements 661 and 662 do not contact each other and exhibit a gap 670 there between, which is adjustable as needed.

As in the other embodiments the sludge is conveyed from the centrifuge 7 to the centrifuge exit 9, which with a speed of approximately 50 m/s is conveyed to the inside 650 of the lysing device 600.

The sludge from the centrifuge 4 first meets the angled surface 651 of the stationary part 630. On the basis of this impacting of the clarified sludge already a number of the present microorganisms cells, such as bacteria and protozoa, rupture.

In order to further increase the lysing impact effect upon the angled outer surface 651, uneven features such as in the form of knives, pins or the like can be provided.

The sludge is then conveyed via channel 652 to the actual cutting unit 656. The knife shaped cutting elements 661 rotate in the exemplary case with a rotating speed of approximately 80 m/s. The sludge is then passed through the cleft 670 between the knives 661 and 662 and must, in the present embodiment, pass by four rows of cutting elements 662, in order to finally reach the sludge exit 695.

On the basis of the rotation speed as well as the design of the cutting device 656 and the cutting elements 651 and 652 enormous shearing forces influence on the microorganisms contained in the sludge, so that the largest part of the therein contained microorganisms cells are shredded, whereby an extreme lysing effect is produced by the cutting unit 605, whereby the majority of the cells contained in the sludge are lysed and release their cytoplasma into the surrounding environment, in order to provide an excellent nutritive medium for the surviving cells, which then lead to an increased bio-gas production and reduction of the amount of sludge.

FIG. 11 shows a section along lines 11—11 in 5 [sic] FIG. 10 from which it can be seen, that in the lysing device 600 also cutting elements 661 or 662 can be employed, of which the ends, in which the exemplary embodiment are knife ends 663, are so designed, that a part of the sludge of the preceding knife part is again fed back or returned, whereby 10 [sic] a certain pumping effect in the direction of the centrifuge results and whereby the shearing force and therewith the lysing effect can be increased even further.

At the exit 695 there is provided a dam 690, of which the height 15 is adjustable and therewith the residence time within the cutting device 656 and therewith the lysing degree is adjustable.

FIG. 12 shows a section along line 12—12 in FIG. 10, from which it can be seen, that the cutting elements 661 20 [sic] and 662 which are provided in the cutting element or knife rows 641, are staggered with respect to each other.

FIG. 13 shows a section view of a pin milling device 705 of a lysing device 700 of an inventive device 1 in a seventh embodiment.

The pin milling device is provided, as in the other illustrative embodiments, as an integral component of the centrifuge 4 at the centrifuge outlet 9. The lysing device 700 and in particular the pin milling device 705 includes a rotating part 720 and a stationary part 730. The stationary part 730 is sealed towards the outside with seals 701.

The rotating part 720 is connected to the jacket 7 of the centrifuge 4. The rotating part 720 of the pin milling device 705 is provided with multiple rows of pins 761, which engage in the entreaties formed by pins 762 and which are provided on the stationary part 730.

In an exemplary case the rotating part 720 and the stationary part 730 respectively each are provided with three pin rows 741.

The pin milling device 705 is closed off towards the outside by a dam 790 and includes a sludge outlet 795.

As in the other embodiments the sludge is conveyed in the direction shown on the arrow through the centrifuge 4 to the centrifuge outlet 9 and enters then into the inside 750 of the lysing device. The sludge is then forced into the interstitial spaces 770 between the individual pins 761 and 762 and is then subject to large shear forces produced by the rotation of pins 761. Similarly to the cutting unit 605 of the lysing device 600, large shear forces occur in the pin milling device 705 between the individual pins 761 and 762 or as the case may be between the individual pin rows 741, which are capable of disrupting cells of the microorganisms contained in the sludge, so that their content is released to the surrounding medium.

The sludge processed with the lysing device 700 then exits through sludge outlet 195 and can as desired be further processed.

The residence time of the sludge and therewith the amount of lysing can be adjusted through the height of the dam 790.

In a preferred embodiment of the present pin milling device 705 the distance or spacing between the two pin rows 741 is adjustable, whereby an even greater shear effect can be produced and therewith a higher lysing level can be achieved.

FIG. 14 shows a section along line 14—14 in FIG. 13.

Particular advantages of the lysing device 700 in the form of a pin milling device 705 lie founded therein, that the residence time is adjustable, the efficiency is easily adjustable for example by the number of pins 761 and 762 and that the individual pins 761, 762 can easily be changed out as necessary.

A further advantage lies in the relatively small constructional space requirement and in relatively large tolerances for the individual pins. As desired it may be useful to provide at the centrifuge outlet 9 or at the inlet to the centrifuge 4 a filter not shown in FIG. 13, in order to retain large foreign bodies, which might lead to damage of pins 761 and 762.

Besides the high shear forces, which occur between the rows of pins 741, the lysing effect is made possible by impacting and battering the cells.

The purification unit shown in FIG. 15 for utilization of a waste water clarification process includes a primary settling tank 802 with an inlet or supply side 801 of raw waste water. The primary sludge 811 is then conveyed to an anaerobic reactor 812. The effluent from the primary settling tank 802 is conveyed to an aerobic biological activation system, the mixture from the activation system 803 is conveyed to a supplemental clarification tank 804, where a settling or separation out of the purified waste water 805 occurs. A part of the settled activated sludge 806 is pumped back with a sludge return pump 820 as conveyance device in the activation system 803. The surplus activated sludge 807 is conveyed to a thickening centrifuge 4 with lysing device 10, where sludge thickening as well as rendering or destroying of cells of a portion of the microorganisms occurs.

The centrate 809 is returned back to the activation system 803. The thickened sludge is conveyed to the anaerobic reactor 812. A reaction mixture 813 from the anaerobic reactor 812 is conveyed to a thickening or dewatering centrifuge 4a, where there occurs the dewatering of the stabilized sludge and the rendering or rupturing of cells of a portion of the microorganisms. The centrate 817 is returned back to the activation system 803 and/or a part thereof is conveyed to the anaerobic reactor 812. The dewatered anaerobically stabilized sludge 815 passes via outlet 818 to a dump and/or a part 816 thereof is returned back to the anaerobic reactor 812.

The part of this system, in which the partial destruction of the cells of the microorganisms occurs, is comprised of the thickening centrifuge 4 and the dewatering centrifuge 4a and/or the return sludge pump 820 and the above mentioned sludge pump. In an exemplary case the lysing device is provided as a friction grinding device 100 with a rotating grinding disk 161 and a stationary grinding disk 162 at the centrifuge 4 while at the outlet 9 of the centrifuge 4a a lysing device 10 in the form of a knife cutting unit 605 is provided.

For the preparation of the stimulating reagent it is also possible to employ on the one hand activated sludge and on the other hand anaerobic stabilized sludge and more particularly either direct from the reactor on hand or from another, effective reactor. In the first indicated case the surplus activated sludge 807 is conveyed to the thickening centrifuge 4 where there occurs, besides the thickening of the sludge, a destruction/lysing of part of the biomass cells in the lysing device, wherein the centrate 809 is returned to the activation device 803 and the thickened part 810 is conveyed to the anaerobic reactor 812 for sludge stabilization. In the other case the anaerobic stabilized sludge 813 is conveyed to the dewatering centrifuge 4a where besides the dewatering of the sludge there occurs a destruction of a part of the biomass cells wherein a portion of 5 to 30% of the centrate 817 and/or a part of the 5 to 30% dewatered sludge 816 is returned back to the anaerobic reactor 812 for sludge stabilizing.

The treatment plant utilizing the process according to the present invention is thus significantly advantageous economically from the perspective of utilization at an the industrial scale in comparison to the state of the art using a separate lysed preparation. In this manner it is possible simultaneously to stimulate the aerobic and anaerobic biological purification processes, and hereby to reduce the amount of sludge to be disposed of and to increase the bio-gas production.

An application of the inventive device or, as the case may be, treatment plant achieves in practice overall an improvement in a series of technical parameters. In the processing of dissolved impurities (anaerobic waste water purification), as well as the anaerobic sludge stabilization one reaches the following results: The output of the anaerobic reactor is increased, the decomposition of organic materials is accelerated, the decomposition of organic materials in the course of the stabilization process is likewise accelerated (in sludge the depth of the anaerobic decomposition, in waste water the possibility of decomposing problematic materials such as, for example, various zenobiotica or poisons), the bio-gas production is increased, the production of stabilized sludge is minimized, the dewatering ability of the anaerobic stabilized sludge is improved and the energy equation of the process in comparison to the conventional design is likewise improved.

EXAMPLE 1

The function as well as the technical utilization according to the invention is to be seen in FIG. 15. As the main unit for preparation of the stimulating reagent, that is, for decomposing or the lysing of a part of the biomass cells of the overflow or surplus activated sludge, a thickening centrifuge 4 is used. For determining the amount of released cell lysate the concentration of the released organismic substances, expressed as $BOD_5$ in the entrance stream 807 and the output stream 810 from the thickening centrifuge 4 is used with the following results:

| | | |
|---|---|---|
| Inlet Stream (807) | $BOD_{5(released)}$ | –140 mg/l |
| Concentrate (Stream 810) | $BOD_{5(released)}$ | –630 mg/l |

With inlet stream 807 and concentrate 810 the tests of the methanogenic activity was carried out. The concentration of the suspended materials was adjusted such that it was the same in both streams. Tests were carried out under the same conditions and with the same inoculum concentration. As inoculum an anaerobic stabilized sludge from a bioreactor was employed. The bio-gas production was determined separately for each stream and for the mixture of both streams with the same amount of total mass. The bio-gas production of the same amount of total material was approximately 10.1% higher in the higher concentrate 110 than by the inlet stream 807. The product results with the mixture produced an increase of approximately 13.3% and approximately 31.2% with respect to the theoretical value depending upon the load of the anaerobic inoculum (0.54 and 0.27 g COD/g organic part in a gram of the not dissolved material (a condition loss)). The theoretical value presents the sum of the production gas value of the same amount for each stream individually.

EXAMPLE 2

Verification of the stimulation influence of the cell lysate on the anaerobic decomposition with simple substances.

Methanogenic activity tests of anaerobic co-fermentation with formic acid, vinegar, propionic acid and glucose were undertaken. In all cases the same inoculum amount was employed, one test series was carried out with addition of thickened surplus of activated sludge concentrate (stream 810) and another with addition of the same amount of inlet surplus activated sludge from the centrifuge (stream 807). The co-fermentation of the complex materials with simple substrates sometimes causes the increase of the decomposition ability of certain components of the complex substrate. The co-fermentation of the same amount of tested sludge with glucose exhibited an increase in the decomposition ability with the inlet sludge to approximately 41.8% and with the concentrate to approximately 51.3% (difference in effect of approximately 11.3%). The co-fermentation with formic acid was only positive at a concentration of 13.5% (difference in effect of approximately 33%).

What is claimed is:

1. A thickening centrifuge for thickening of surplus sludge (807), wherein said sludge contains organisms, and wherein a lysing device is integrated in said thickening centrifuge (4) for rupturing cells of organisms contained in said sludge.

2. A thickening centrifuge according to claim 1, wherein said lysing device comprises at least one milling device and/or rasping device.

3. A thickening centrifuge according to claim 2, wherein the thickening centrifuge (4) comprises a rotating conveyor device (6) which conveys the sludge to a sludge outlet (9).

4. A thickening centrifuge according to claim 3, wherein said rotating conveyor device (6) is a screw conveyor.

5. A thickening centrifuge according to claim 3, wherein the thickening centrifuge (4) further comprises a rotating jacket (7), and wherein the jacket (7) and the conveyor device (6) rotate with different rotational speeds.

6. A thickening centrifuge according to claim 2, wherein the thickening centrifuge (4) comprises a rotating jacket (7).

7. A thickening centrifuge according to claim 2, wherein the thickening centrifuge (4) is a jet centrifuge or a jet separator.

8. A thickening centrifuge for thickening of surplus sludge (807), wherein said sludge contains organisms, wherein a lysing device is integrated in said thickening centrifuge (4) for rupturing cells of organisms contained in said sludge, and wherein the lysing device (10; 100; 200; 300; 400; 500; 600; 700) is a friction grinding device (100; 200).

9. A thickening centrifuge according to claim 8, wherein the friction milling device (100; 200) comprises at least one grinding disk (161, 162) having a grinding surface for grinding the sludge and cells of the organisms contained in the sludge.

10. A thickening centrifuge according to claim 9, wherein at least one of said grinding disks exhibits recesses (163) at its grinding surface (164, 165).

11. A thickening centrifuge according to claim 10, wherein said recesses (163) exhibit an angle of incidence with respect to the radial direction.

12. A thickening centrifuge according to claim 10, wherein said recesses are grooves interrupted by non-recessed regions in the grinding surface (164, 165), thereby forming radial groove rows.

13. A thickening centrifuge according to claim 12, wherein adjacent groove rows are staggered so that in regions, in which a groove row is interrupted, the adjacent groove row does not exhibit an interruption.

14. A thickening centrifuge according to claim 8, wherein a the friction milling device comprises a rotating grinding disk (161) and a stationary grinding disk (162), wherein said rotating grinding disk (161) rotates together with the jacket (7) of the thickening centrifuge and against said stationary grinding disk (162), and wherein the space (170) between the two grinding disks (161, 162) is adjustable.

15. A thickening centrifuge according to claim 14, wherein said space (170) between the two grinding disks (161, 162) is adjustable in the range of approximately 0.5 to 5 mm.

16. A thickening centrifuge according to claim 14, wherein the lysing device has an inlet and an outlet, and wherein the lysing device is provided with a dam (190) at its sludge outlet.

17. A thickening centrifuge according to claim 8, wherein the friction grinding device (100; 200) comprises a grinding cone (205) for grinding the sludge and cells of the organisms contained in the sludge.

18. A thickening centrifuge according to claim 17, wherein the grinding cone (205) comprises a rotating outer cone (220) with at least one grinding surface (261) and an inner cone (230) which has at least one surface (262) opposing said outer cone grinding surface (261).

19. A thickening centrifuge according to claim 18, wherein said inner cone (230) is stationary.

20. A thickening centrifuge according to claim 18, wherein at least the rotating outer cone (220) has recesses (263) on its grinding surface (261).

21. A thickening centrifuge according to claim 20, wherein said recesses are notches, wherein the breadth of the notch is the same as the depth of the notch.

22. A thickening centrifuge according to claim 21, wherein the notches are interrupted by non-recessed areas of the grinding surface (261, 262).

23. A thickening centrifuge according to claim 22, wherein adjacent lying notch rows are staggered, so that in areas in which a notch row is interrupted, the adjacent notch row is not interrupted.

24. A thickening centrifuge according to claim 22, wherein inner and outer cones (230, 220) are positioned separated (270) with respect to each other, and wherein the separation distance (270) is adjustable.

25. A thickening centrifuge according to claim 24, wherein the separation distance (270) is adjustable during rotation or while stationary via a bearing surface (275) and springs.

26. A thickening centrifuge for thickening of surplus sludge (807), wherein said sludge contains organisms, wherein a lysing device is integrated in said thickening centrifuge (4) for rupturing cells of organisms contained in said sludge, and wherein the lysing device (10; 100; 200; 300; 400; 500; 600; 700) is constructed as a profile rasp (305).

27. A thickening centrifuge according to claim 26, wherein the profile rasp (305) comprises a stationary outer hull (330) and a rotating rasp surface (320), said rasp surface including a grinding surface, wherein the distance (370) between outer hull (330) and rasp surface (320) is adjustable.

28. A thickening centrifuge according to claim 27, wherein the rotating rasp surface (320) is provided with recesses (363).

29. A thickening centrifuge according to claim 28, wherein said recesses (363) are wave shaped recesses (363).

30. A thickening centrifuge according to claim 28, wherein the recesses (363) exhibit an angle of incidence to the direction of rotation to the profile rasp (305).

31. A thickening centrifuge according to claim 27, wherein the lysing device has a sludge inlet and a sludge outlet, and wherein the grinding surface (305) of the profile rasp has a part (326) extending in the direction of the sludge outlet (395) and a part (325) extending in the opposite direction, wherein the part (326) extending in the direction of the sludge outlet (395) exhibits a greater separation from the wall of the outer hull (330) than the part (325) extending in the opposite direction.

32. A thickening centrifuge according to claim 27, wherein the distance (370) between the rasp surface (320) and outer hull (330) is minimally approximately 2 mm to maximally approximately 10 mm.

33. A thickening centrifuge according to claim 26, wherein the profile rasp (305) includes a central inlet for sludge.

34. A thickening centrifuge for thickening of surplus sludge (807), wherein said sludge contains organisms, and wherein a lysing device is integrated in said thickening centrifuge (4) for rupturing cells of organisms contained in said sludge, wherein the lysing device (10; 100; 200; 300; 400; 500; 600; 700) is constructed as a roller crusher (405).

35. A thickening centrifuge according to claim 34, wherein the roller crusher (405) comprises an outer hull (430) having an inner wall, and at least one roller set (441, 442) which rolls upon the inner wall of the outer hull (430).

36. A thickening centrifuge according to claim 35, wherein said outer hull is stationary.

37. A thickening centrifuge according to claim 35, wherein the roller set (441, 442) comprises at least ten rollers.

38. A thickening centrifuge for thickening of surplus sludge (807), wherein said sludge contains organisms, wherein a lysing device is integrated in said thickening centrifuge (4) for rupturing cells of organisms contained in said sludge, and wherein the lysing device (10; 100; 200; 300; 400; 500; 600; 700) is constructed as a passing drum (505).

39. A thickening centrifuge according to claim 38, wherein the passing drum (505) comprises a stationary outer hull and multiple passing elements which rotate within a stationary outer hull.

40. A thickening centrifuge according to claim 39, wherein the spacing (570) between the multiple passing elements and the inner wall of the outer hull (530) is adjustable.

41. A thickening centrifuge for thickening of surplus sludge (807), wherein said sludge contains organisms, wherein a lysing device is integrated in said thickening centrifuge (4) for rupturing cells of organisms contained in said sludge, and wherein the lysing device (10; 100; 200; 300; 400; 500; 600; 700) is constructed as a cutting unit (605).

42. A thickening centrifuge according to claim 41, wherein the cutting unit (605) comprises rotating cutting elements (641) and stationary cutting elements, wherein the cutting elements (641) engage within each other without however touching each other.

43. A thickening centrifuge according to claim 42, wherein the rotating cutting elements (641) are rows of knives (641), and wherein the stationary cutting elements are rows of knives (641).

44. A thickening centrifuge according to claim 43, wherein the knives (661, 662) rotate with a speed of approximately 50–100 m/s.

45. A thickening centrifuge according to claim 43, wherein the knife rows (641) comprise a plurality of knives (661, 662), wherein adjacent situated knife rows are staggered so that in the areas, in which a knife row (661, 662) is interrupted, the adjacent knife row (641) is not interrupted.

46. A thickening centrifuge according to claim 43, wherein the knife rows (663) exhibit an angle of incidence to the rotation direction of the cutting unit (605).

47. A thickening centrifuge according to claim 43, wherein the spacing (670), the height and the circumference position of the knives of the stationary and the rotating knife rows (641) are adjustable.

48. A thickening centrifuge according to claim 42, wherein the device is provided with a dam (690) at its sludge outlet (695).

49. A thickening centrifuge according to claim 48, wherein the lysing device has an inlet and an outlet, and wherein the height of the dam (690) is adjustable at the sludge outlet (695).

50. A thickening centrifuge for thickening of surplus sludge (807), wherein said sludge contains organisms, wherein a lysing device is integrated in said thickening centrifuge (4) for rupturing cells of organisms contained in said sludge, and wherein the lysing device (10; 100; 200; 300; 400; 500; 600; 700) is constructed as a pin milling device (705).

51. A thickening centrifuge according to claim 50, wherein said lysing device has a sludge inlet and a sludge outlet, wherein the pin milling device (705) comprises rotating rows of pins (761; 741) rotating about an axis, stationary rows of pins (762; 741), as well as a dam (790) at the sludge outlet (795), wherein the rotating and the stationary rows of pins (761, 741) engage within each other without however contacting each other.

52. A thickening centrifuge according to claim 51, wherein the space (770) between the stationary and the rotating pins (761, 762) is adjustable.

53. A thickening centrifuge according to claim 51, wherein the rotating pins (761) rotate with a speed of approximately 50–100 m/s.

54. A thickening centrifuge according to claim 51, wherein the rows of pins (761, 762) are arranged such that adjacent situated pin rows (741) are staggered, such that in regions in which no pins are present in a pin row (741), the adjacent pin row (741) is provided with pins (761, 762).

55. A thickening centrifuge according to claim 51, wherein the pins of the pin rows (761, 762) are provided at an angle with respect to the axis of rotation.

56. A thickening centrifuge according to claim 51, wherein a dam (790) is provided at the sludge outlet (795), and wherein the height of said dam (790) is adjustable at the sludge outlet (795).

57. A process for minimizing the amount of decayed or residual sludge produced by treatment plants, said process comprising the following steps:

allowing waste water to settle in at least one settling tank (802) to form settled surplus sludge (807) and solids-reduced waste water;

thickening the surplus sludge (807) from the settling tank (804) by passing through at least one thickening centrifuge (4), wherein approximately 0.5 to 50% of the amount of the micro-organism cells originally contained in the surplus sludge (807) are lysed in the thickening centrifuge (4) during the thickening;

conveying the lysed thickened settled surplus sludge (807) to at least one anaerobic reactor (812) by means of at least one conveyance device;

anaerobic converting said thickened settled surplus sludge (807) in said at least one anaerobic reactor (812);

conveying the solids-reduced waste water following settling to an aerobic activation device (803); and aerobic conversion of the solids-reduced waste water in said at least one aerobic activation device (803).

58. A process according to claim 57, wherein said anaerobic reactor (812) produces a combustible gas.

59. A process according to claim 58, wherein said combustible gas is methane.

60. A process according to claim 58, wherein said combustible gas produced in the process is used for production of electricity.

61. A process according to claim 60, wherein the electricity produced is employed for powering the treatment plant.

62. A process according to claim 58, wherein the thickening in the centrifuge and lysing in the lysing device act on the sludge and organisms to synergistically increase the volume of gas produced in said step of anaerobic conversion by 10–50%.

\* \* \* \* \*